(12) United States Patent
Weaver et al.

(10) Patent No.: US 9,935,765 B2
(45) Date of Patent: *Apr. 3, 2018

(54) DEVICE, SYSTEM AND METHOD FOR SECURING AND COMPARING GENOMIC DATA

(71) Applicant: GENFORMATIC, LLC, Austin, TX (US)

(72) Inventors: Daniel Weaver, Austin, TX (US); Justin MacCarthy, Dublin (IE); Stephen Ayers, Houston, TX (US); Justin Reese, Milledgeville, GA (US)

(73) Assignee: GENFORMATIC, LLC, Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/269,611

(22) Filed: Sep. 19, 2016

(65) Prior Publication Data

US 2017/0005787 A1 Jan. 5, 2017

Related U.S. Application Data

(63) Continuation of application No. 14/356,137, filed on May 2, 2014, now Pat. No. 9,449,191.

(60) Provisional application No. 61/555,342, filed on Nov. 3, 2011, provisional application No. 61/608,084, filed on Mar. 7, 2012.

(51) Int. Cl.
*G06F 21/00* (2013.01)
*H04L 9/00* (2006.01)
*G06F 21/62* (2013.01)
*G06F 19/22* (2011.01)
*G06F 19/28* (2011.01)
*G06F 19/00* (2018.01)

(52) U.S. Cl.
CPC .............. *H04L 9/008* (2013.01); *G06F 19/22* (2013.01); *G06F 19/28* (2013.01); *G06F 19/3431* (2013.01); *G06F 21/6245* (2013.01)

(58) Field of Classification Search
CPC .............................. G06F 19/22; G06F 21/6245
See application file for complete search history.

(56) References Cited

U.S. PATENT DOCUMENTS

| | | | | |
|---|---|---|---|---|
| 2007/0271604 A1* | 11/2007 | Webster | .............. | G06F 21/6245 726/10 |
| 2013/0318351 A1* | 11/2013 | Hirano | .................. | H04L 9/3073 713/168 |
| 2014/0310215 A1* | 10/2014 | Trakadis | ................. | G06F 19/28 706/13 |

\* cited by examiner

*Primary Examiner* — Ghazal Shehni
(74) *Attorney, Agent, or Firm* — Polsinelli PC; Andrew Z. Weaver

(57) ABSTRACT

The present disclosure presents methods, systems, and devices for encrypting and comparing genomic data. The comparison of genomic data allows the owner of the data to ensure security of the data even when the party conducting the comparison is beyond the control of the owner of the data. The encryption of the genomic data enables the transmission, storage, and use of the genomic data in a secure media.

18 Claims, 13 Drawing Sheets

DEVICE, SYSTEM AND METHOD FOR SECURING AND COMPARING GENOMIC DATA

CROSS REFERENCE TO RELATED APPLICATIONS

The present application is a continuation of U.S. application Ser. No. 14/356,137, filed May 2, 2014, which is the national phase under 35 U.S.C. § 371 of PCT International Application No. PCT/US2012/063624, filed Nov. 5, 2012, which claims the benefit and priority to U.S. Provisional Application No. 61/608,084, filed Mar. 7, 2012, and U.S. Provisional Application No. 61/555,342, filed Nov. 3, 2011. Each of the above identified applications is hereby incorporated by reference in the entirety.

FIELD

The present disclosure relates to securing and/or comparing genomic data. Specifically, encryption of genomic data is presented. Additionally, a comparison technique is presented to determine similarities between two sets of genomic data.

BACKGROUND

Genomic data has become increasingly easy and cost effective to produce and genomic data is accumulating with considerable velocity. At the same time, the medical, social and personal utility of genomic information is expanding, revealing new and potentially transformative applications of genomic technology. Simultaneously, genomic data is inherently sensitive—potentially allowing third parties to learn about health risks, family history and important personal attributes (e.g., probable hair color, eye color, and other phenotypic information) of individuals whose genomic data becomes compromised. Moreover, genomic data is inherently personally identifiable, posing the risk that third parties will be able to learn the identity of individuals whose genomic data is compromised (and by extension, important information about the identity of family members and their genetically encoded traits). This personal security vulnerability may enable curious data interceptors to obtain information about the intercepted individual and her family, including for instance, family medical risk predisposition, probable lifespan or potential response to medical therapy. An individual may go to a lab and have specimen taken for the purpose of producing genomic data. This genomic data can be stored and transmitted to others by health care providers, healthcare institutions, third party entities or the individual. Furthermore, users can decide to share or compare genomic data for a variety of medical and non-medical reasons and this is increasingly probable as the power of genomic data to produce meaningful insights into phenotypic features, probable drug safety and efficacy responses or a variety of other genomic correlates grows.

BRIEF DESCRIPTION OF THE DRAWINGS

Implementations of the present technology will now be described, by way of example only, with reference to the attached figures, wherein.

DETAILED DESCRIPTION

Figure 1:
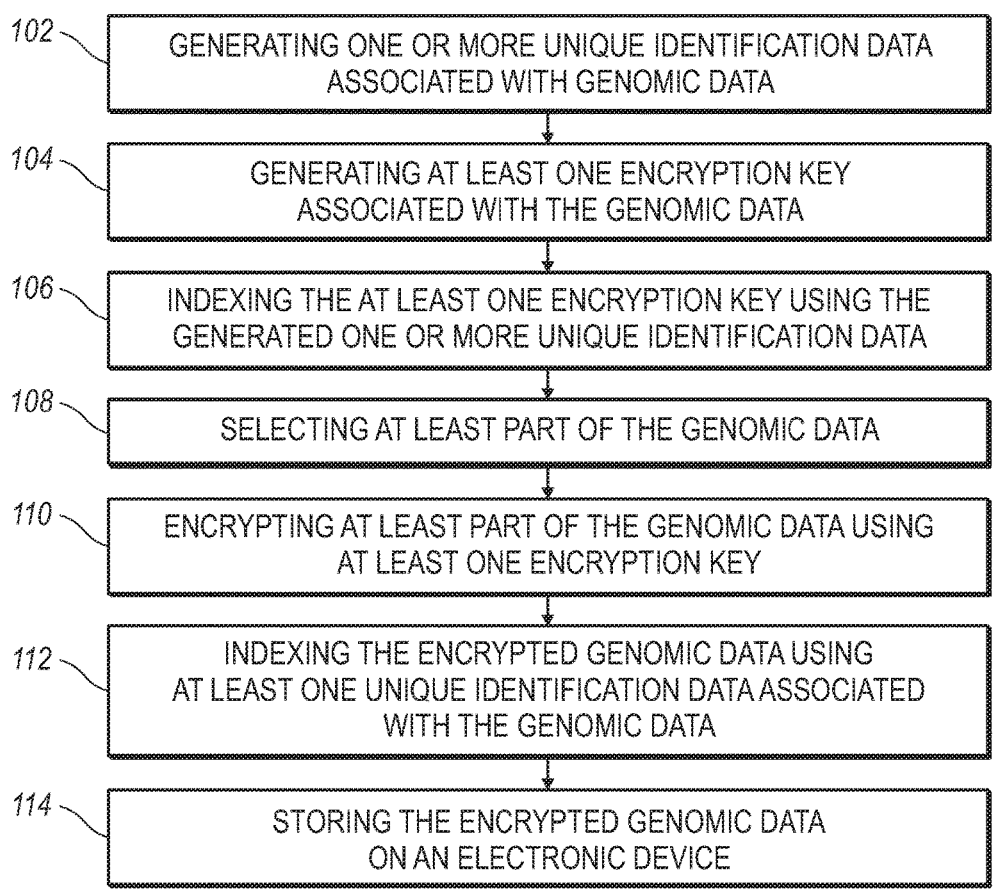
FIG. 1 is a flow chart illustrating a coding scheme according to one example implementation.

For simplicity and clarity of illustration, where appropriate, reference numerals have been repeated among the different figures to indicate corresponding or analogous elements. In addition, numerous specific details are set forth in order to provide a thorough understanding of the implementations described herein. However, those of ordinary skill in the art will understand that the implementations described herein can be practiced without these specific details. In other instances, methods, procedures and components have not been described in detail so as not to obscure the related relevant feature being described. Also, the description is not to be considered as limiting the scope of the implementations described herein.

Several definitions that apply throughout this disclosure will now be presented.

Function may refer to or comprise one of a mathematical operation, an algorithm, a set of instructions to a processor or computer, an encryption scheme comprised of multiple logic gates, logical operations, mathematical data transformations or data processing operations, or where the context is appropriate some combination of any of the above.

Protocol may refer to or comprise one of a standard agreement among two or more devices about the rules of communication between or among them and how they communicate, a scheme or fixed set of mathematical operation, a fixed or standard set of procedures or processes to transform or otherwise manipulate or perform mathematical or logical operations on data, or where the context is appropriate some combination of any of the above.

A sample may refer to or comprise one of a biological specimen including but not limited to specimen emanating from or representing one or more microorganisms, virus, organism, cell, gamete, sperm, egg, oocyte, germ cell, somatic cell, stem cell, tissue, culture, tumor, neoplasm, organ, organ system, organism, individual or any combination of them, all or part of one or more nucleic acid extraction, DNA molecule, RNA molecule, genome sequence, transcriptome sequence or other biochemical or molecular constituents emanating from or representing one or more biological specimen, organism, individual or any combination of them, a nucleic acid sequence, genome sequence, genotype, DNA sequence, RNA sequence, or any chemically or physically modified form of any of them, or any combination thereof, including but limited to synthetic or engineered forms of any of any molecule, biochemical, genome sequence, nucleic acid sequence, transcriptome sequence, virus, microorganism, cell, tissue, organ, system, gamete, oocyte, sperm, embryo, fetus, neonate or individual, or any data representing or associated with or emanating from any of them, regardless of the means or methods of data generation.

Genomic data is data that can be one or more of the following: the genome or exome sequence of one or more, or any combination or mixture of one or more, mitochondrion, cell, tissue, neoplasm, tumor, organ, organism, microorganism, virus or individual, or the genome sequence or exome sequence of one or more samples comprised of any combination or mixture of mitochondria, cells, tissues, neoplasms, tumors, organs, microorganisms, organisms or individuals, and further including but not limited to nucleic acid sequence information, genotype information, gene expression information, genetic data, epigenetic information including DNA methylation, acetylation or similar DNA modification data, RNA transcription, splicing, editing or processing information, or medical, health or phenotypic data, or nutritional, dietary or environmental condition or exposure information or other attribute data of any microorganism, virus, cell, tissue, neoplasm, tumor, organ, organ system, sample, individual or group of samples or individuals.

An electronic device as described herein is a device which includes a processor and memory. The memory can be either transitory or non-transitory as described below. Examples of electronic devices include desktops, laptops, servers, tablets, smartphones and personal digital assistants.

The present disclosure generally concerns the processing and handling of genomic data. In at least one embodiment, the present disclosure presents devices, systems, and methods for the encryption or coding of genomic data. The encryption or coding of genomic data can be performed on one or more electronic devices. In at least one implementation, the encryption or coding of the genomic data can be performed via a cloud or other network of computers.

The present disclosure also includes devices, systems, and methods for one or more of the following: compressing, encrypting, decrypting, storing, transmitting, indexing or conducting analyses on nucleic acid sequence information, other genomic, genotypic, genetic, medical, health or phenotypic data. The data will be hereinafter referred to as genomic data. The compression, encryption, decryption, storage, transmission, index, and analysis can be performed on data that is obtained in a variety of different ways and can be performed independently of the method of storage. As explained below, the present disclosure can be implemented on a variety of different hardware architectures. The different architectures can be associated with individual advantages especially due to the proliferation and individualization of the genomic data.

Information generated by sequencing human, animal and plant genomes has and continues to revolutionize many disciplines. Computational processing of genome sequence data and bioinformatic analysis of genomic information are essential aspects of genomic information technology, and are have or will become necessary tools of scientific investigation in many fields, including but not limited to biology, medicine, genetics, animal science, plant science, anthropology, forensic science, personal identification systems and identification verification systems. As new technologies and means of generating nucleic acid sequence data have been developed in the course of the Human Genome Sequencing Project, the costs of genome sequencing has been declining at a rate faster than Moore's Law, and genome sequencing is increasingly common as a tool for scientific research in all fields that involve any aspect of biology, especially medical and pharmaceutical research and investigational and clinical medicine. Genome technology revolutionized biological research, and the accelerating application of genomic sequencing to medical research will revolutionize all of medicine as well. As the clinical utility of genome sequence information becomes more obvious, and the demand for routine genomic sequencing accelerates, the resulting deluge of genomic sequence information will pose enormous data analysis and storage challenges.

Not least among the challenges posed by the need to quickly analyze large amounts of data associated with each subject, is the need to securely manage, store, transmit, share, analyze and/or utilize genomic data. Current regulatory and legal frameworks in many jurisdictions around the world require that human health care information be treated as private information demanding confidentiality, preservation of doctor-patient privileged information. Elimination of personally identifiable information from health care records is usually required in contexts where sensitive health information is compiled, shared, transmitted or used and public disclosure is possible and/or probable. For example, the contexts can include but are not limited to many areas of health and medical research, where redaction of personally identifiable information is required by statute, rule, institutional review board policy and/or practice. Much important medical research requires comparing or correlating genomic markers (e.g., single nucleotide polymorphisms or genomic structural variation) with disease propensity or incidence. Such epidemiological or whole genome disease association research will increasingly utilize complete genomic sequence information from a hundreds or thousands of subjects (often, individuals) with a common condition, attempting to identify genome sequence features that predispose to development of disease or predict drug efficacy or safety. Moreover, the results of that genome sequence association research will soon become a part of regular clinical practice in many fields. Patients will undergo genome sequencing and genome sequence analysis, identifying genomic features that will affect a patient's diagnosis, prognosis and/or therapeutic regimen. The present disclosure presents systems, methods, and devices that allow the sequence information generated, analyzed, stored and/or transmitted in the course of that work to be secure and confidential.

At least one problem of properly securing genomic information and protecting it from unauthorized access and utilization is accentuated by the special risks and potential consequences of unauthorized disclosure of genomic information. Each subject's genome is unique, constituting the digital genetic 'fingerprint' of the subject from which it was derived. No two subjects have the same genomic sequence, and it will soon be possible to use genomic sequence information to identify the subject from whom the sequence was generated. In fact, genomic sequence information is not only the perfect identification technology, it also conveys a great deal of other information that could be used discriminate and classify subjects to their economic, social or medical detriment.

Genomic sequence information can reveal a variety of personal information including but not limited to race or ethnic origin, family history including probable health risks faced by the sequenced person or her family, such as the relative risk or likelihood of developing a wide variety of medical conditions or diseases; whether the individual's actual or potential offspring might develop particular medical conditions or disease; or the probable efficacy or safety of medication or other therapies.

Forensic and security applications for the present technology also abound. Existing and future security screening technologies can utilize genomic sequence information to create identity matrices that enable credentialing confirmation, permission certification and/or verification. Genomic information could be used to permit access, control entry or warn of intrusion in both physical and virtual spaces. Transportation and other public or private security screening will likely depend upon increasingly complex and inherently reproducible unique identifier information, and genomic sequence information is the one of the most naturally complex but unique measurements of identity possible.

As but one example, if genomic information, operating as a surrogate identity profile, becomes public (analogous to fingerprint and photographic and name information for an individual being published) then it would be possible for actors to develop synthetic mimetic oligonucleotides (analogous to a fake passport) containing unique genomic sequence identifiers, and thereby masquerade as the one whose genomic sequence and identity has been compromised or publicly revealed.

Likewise, law enforcement databases will likely wish to control public access to genomic sequence database information that inherently identifies suspects and crime victims alike.

Security vulnerabilities and potential adverse consequences of storing, sharing, comparing genomic data using plaintext genomic information are present and the present technology addresses these problems. The present technology addresses security and vulnerability problems and preserves the ability of individuals and their physicians or health care providers to effectively use genomic information, without exposing that genomic information to exploitation by third parties.

The present technology allows for encoding, encrypting or otherwise transforming the data into a form that can be shared and/or secured without threats to the subject to whom the genomic data belongs. Additionally, the transformation present herein does not create expensive processing bottlenecks, time delays on analysis and utilization of genomic sequence information, and/or impose expensive system administration oversight and expense to implement. The present technology can provide a comprehensive system, method, and device for securely and confidentially managing genomic sequence information efficiently and quickly. Moreover, the present technology preserves rapid processing and analysis capabilities for genomic information and imposes minimal user burdens in time and expense.

Figure 2:
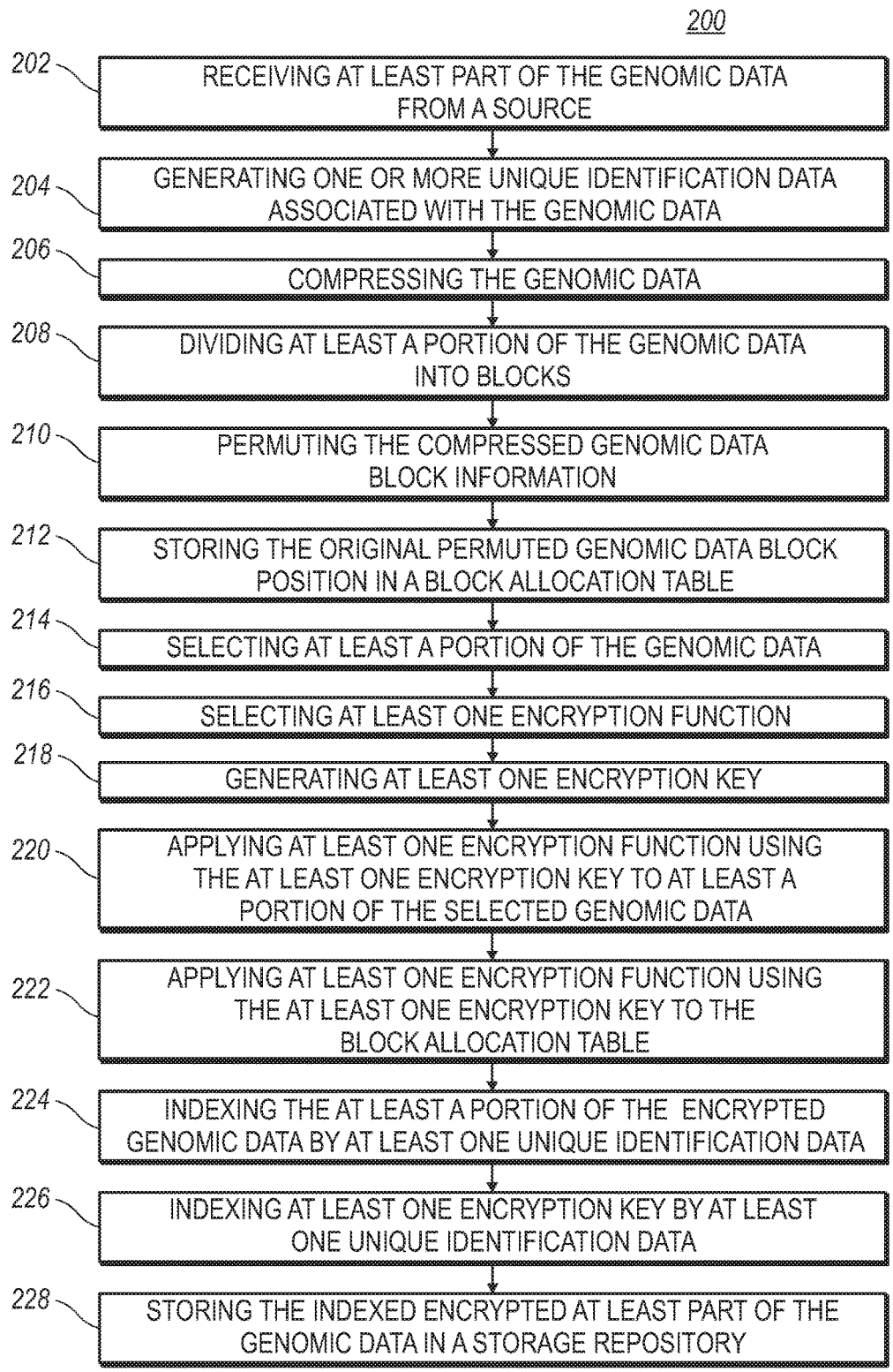
FIG. 2 is a flow chart illustrating a coding scheme according to another example implementation.

Examples of the present technology are illustrated in FIGS. 1 and 2. FIG. 1, presents a method 100 for processing genomic data on an electronic device. The method 100 can include one or more of the steps as presented in FIG. 1. Furthermore, the method 100 can include additional steps which are not illustrated. While the method 100 is arranged in a particular order, the order of the steps can be different in other embodiments.

The method 100 can include generating one or more unique identification data associated with genomic data (102). The genomic data can be one or more of the types of genomic data as described above. The genomic data can be received from at least one source. The at least one source can be at least one of a sample, an individual, or an organism. In yet another implementation, the at least one source can be removed from the actual organism and can be a processing center or other recipient of the sample. The processing center can output genomic data that in turn can be used to generate the one or more unique identification data. The genomic data can be stored on a memory or other media as described herein, one of which is a non-transitory media. The output and other parts of this method can likewise be stored on memory or media, including non-transitory memory or media.

The one or more unique identification data (102) can be one of an arbitrary alphanumeric bit string, a sequence of digits, a sequence of letters, a pseudo-random output of a function operating on input, a pseudo-random number generator comprised of a function operating on an input as modified with an initialization vector, a public encryption key of an individual or an entity, a private encryption key of an individual or an entity, a combination of a public and private encryption key generated by operation of a function, a person's or entity's identification number or other special identifier, a sample ID, a health record ID, a medical record ID, a healthcare system's identification data, a passport number, a driver's license number or any other data intended to be uniquely associated with a physical sample, person, entity, data record, device, computer or any combination of two or more of the above.

Additionally, the generation of the one or more unique identification data can be generated by an electronic device. For example, the processor of the electronic device can generate the one or more unique identification data. In other embodiments, when a server is implemented, the server can generate the one or more unique identification data. In yet other embodiments, the cloud can be used to generate the one or more unique identification data. Likewise, the remainder of the method steps as described herein in regard to any of the methods can be implemented on a single electronic device, on a server, a cloud, or some combination thereof.

In yet other implementations, the one or more unique identification data can be generated by a function. In yet other implementations, the one or more unique identification data can be generated and assigned by an organization, government agency or other entity.

The method 100 can further include generating at least one encryption key associated with the genomic data (104).

The method 100 can further include indexing the at least one encryption key using the generated one or more unique identification data (106).

The method 100 can further include selecting at least part of the genomic data (108).

The method 100 can include the selecting at least part of the genomic data by operation of a function on the genomic data (108).

The method 100 can include the selecting at least part of the genomic data by adherence to a protocol as applied to the genomic data (108).

The method 100 can further include encrypting at least part of the genomic data using at least one encryption key (110).

The method 100 can further include indexing the encrypted genomic data using at least one unique identification data associated with the genomic data (112).

The method 100 can further include storing the encrypted genomic data on an electronic device (114).

In yet other embodiments, the method can further include compressing the genomic data prior to encryption. When the genomic data is compressed prior to encryption it allows for additional space saving and further reduction in processing time. The compressing the genomic data can include applying run length encryption.

The method can further include transmitting at least part or a portion of the encrypted genomic data. The at least part or portion of the encrypted genomic data can be further used for comparison or other processes.

In still other implementations, the method can further include dividing at least a portion of the genomic data into blocks. The method can further include generating genomic block data in response to indexing at least part of the genomic data in at least some data block by one of a genomic coordinate, an order, or genomic data content information. The method can further include storing at least part of the genomic block data in a block allocation table. The method can further include generating at least one encryption key for the block allocation table. The method can further include encrypting the block allocation table using the at least one encryption key. The method can further include generating at least one encryption key for the genomic block data. The method can still further include encrypting at least part of the genomic block data using the at least one genomic block data encryption key. These steps can be implemented alone, in combination with one or more of the method steps as described above, or with all of the method steps where possible.

The method can further include applying a function to divide the genomic data into blocks. Still further the method can include compressing the genomic block data. Additionally, the method can include permuting at least part of the genomic block data. The method can further include indexing the at least part of the genomic data by the permuted genomic block data. Still further, the method can include mapping at least part of the permuted genomic block data to the genomic block data. The method also can include storing the mapping data for each permuted genomic block in the block allocation table. The method can further include encrypting the mapping data for each permuted genomic block.

The method can further include transmitting the at least one block allocation table and one block allocation table encryption key to a receiver; and/or transmitting at least part of the genomic block data, and at least one genomic block data encryption key to a receiver.

The method can further include one or more of the following: receiving the at least one block allocation table encryption key from a sender; receiving at least part of the block allocation table from a sender; receiving at least part of the genomic block data from a sender; receiving at least one genomic block data encryption key from a sender.

The method can further implement one or more of the above steps in a recursive application. The above method steps can be implemented in any combination or order.

FIG. 2 presents a method 200 for processing genomic data on an electronic device. The method 200 can include one or more of the steps as presented in FIG. 2. Furthermore, the method 200 can include additional steps which are not illustrated. While the method 200 is arranged in a particular order, the order of the steps can be different in other embodiments.

The method 200 can include receiving at least part of the genomic data from a source (202).

The method 200 can include at least one embodiment wherein the source of genomic data is a sample (202).

The method 200 can include at least one embodiment wherein the source of the genomic data is an electronic device (202).

The method 200 can include at least one embodiment wherein the source of the genomic data is a device that generates genome sequence data, transcriptome sequence data or other nucleic acid sequence or genotype data (202).

The method 200 can further include generating one or more unique identification data associated with the genomic data (204).

The method 200 can further include compressing the genomic data (206).

The method 200 can further include dividing at least part of the compressed genomic data into blocks (208).

The method 200 can further include permuting the genomic data represented within data blocks by mixing, merging or shifting the data comprising genomic data blocks or shuffling the order or position or genomic coordinates of one or more data blocks to randomize the data block order, position or processing priority while preserving the data content of the one or more data blocks (210).

The method 200 can further include at least one embodiment wherein the permuting or shuffling of the compressed genomic data block position or order is accomplished by application of a function or protocol to the genomic block order or position or processing priority (210).

The method of 200 can further include at least one embodiment wherein the permuting or shuffling of the compressed genomic block data is accomplished by means of application of a function or protocol to the genomic block data.

The method 200 can further include storing the original and permuted genomic data block position or order data in a block allocation table (212).

The method 200 can further include selecting at least part of the genomic data (214).

The method 200 can further include at least one embodiment wherein the selecting is the result or output generated by application of a function to the genomic data (214)

The method 200 can further include selecting at least one encryption function (216). In at least another embodiment, the method can further include selecting at least one encryption protocol instead of the at least one encryption function. In other embodiments, the selecting can include at least one encryption function and at least one encryption protocol. An encryption function as referred to herein can be a transformation of data based upon instructions executing on a processor that allows the processor to transform the data. An encryption protocol can be a predetermined routine that allows one or more electronic devices to communicate with each other using the encryption protocol. The encryption protocol can be implemented when one or more electronic devices are configured to communicate with each other. In at least one implementation, the selected encryption protocol or function can be a garbled circuit protocol. In yet another implementation, the selected encryption function or protocol can be a cryptographic hash function. In still another implementation, the selected encryption function or protocol is a homomorphic encryption protocol. In yet another implementation, the selected encryption function is a one-way compression function.

The method 200 can further include generating at least one encryption key (218).

The method 200 can further include generating at least one encryption key using an asymmetric key protocol.

The method 200 can further include generating at least one encryption key using a hybrid key protocol.

The method can further include generating at least one encryption key using a symmetric key protocol.

The method 200 can further include applying at least one encryption function using the at least one encryption key to at least part of the selected genomic data (220).

The method 200 can further include applying at least one encryption function using at least one encryption key to the block allocation table (222).

The method 200 can further include at least one embodiment wherein the at least one encryption function applied to the genomic data is a homomorphic encryption function (220).

The method 200 can further include at least one embodiment wherein the at least one encryption function applied to the block allocation table is a homomorphic encryption function (222).

The method 200 can further include at least one one embodiment wherein the at least one encryption function applied to the genomic data is a cryptographic hash function (220).

The method 200 can further include at least one embodiment wherein the at least one encryption function applied to the block allocation table is a cryptographic hash function (222).

The method 200 can further include indexing the at least part of the encrypted genomic data or the encrypted block allocation table by at least one unique identification data (224).

The method 200 can further include indexing at least one encryption key by at least one unique identification data (226).

The method 200 can further include storing the indexed, encrypted at least part of the genomic data in a database or memory (228).

In another embodiment, which can implement the coding as described above, the present disclosure enables the comparison of two or more sets of genomic data. As indicated above genomic data can be produced and stored on an electronic device. In some instances, it is desirable to share the genomic data with one or more individuals in which confidentiality may not exist. For example, a person can decide that they wish to determine the degree to which they are related with another person. The transmission and storage of the genomic data might cause the person to decide that they will not share the data. As presented herein, the present disclosure presents devices, systems, and methods for sharing and comparing of genomic data. The example of comparing genomic data to determine the degree of relatedness is just an example. The genomic data can be compared to determine the degree of sequence or genotype similarity or genome homology, infer inbreeding, assess risk of producing unhealthy offspring, assess offspring's probable risk for developing specific medical conditions, assess probable phenotype of offspring, determine disease states, predict susceptibility to disease, diagnose disease, assess probable drug safety or efficacy, infer medical prognosis, assess probable therapeutic efficacy or safety, predict healthcare outcomes, conduct forensic sample comparisons and investigations, and infer ethnicity, among other useful things. Additionally, a person can use one or more relative's genomic data to accomplish many of the same risk and probable outcome assessments, including disease predisposition, health status, and ethnicity, among other things.

The method can further include transmitting at least a portion of the encrypted genomic data to a recipient; and/or transmitting at least one encryption key to a recipient. The recipient can be another electronic device. The recipient electronic device can be controlled by a party different from the party to whom the genomic data belongs. The source of the genomic data can be information in a database in an electronic device; and wherein the computer readable medium comprises or represents genomic data in database in an electronic device.

The methods as presented in regards to FIGS. 1 and 2 above can further include one or more of the following steps. The methods can further optionally include one or more of the following steps: choosing at least one function to generate a list or set of specified genomic data sections or multiple portions of the genomic data; applying the selected function or protocol to generate a list or set of specified genomic data sections or multiple portions of the genomic data; storing the list or set of genomic data sections, or multiple portions of the genomic data and the data selection function in a computer readable medium. Additionally, the methods can further include transmitting the genomic data selection function to a recipient. The recipient electronic device can be controlled by a party different from the party to whom the genomic data belongs. The source of the genomic data can be information in a database in an electronic device; and wherein the computer readable medium comprises or represents genomic data in database in an electronic device. In yet another embodiment, the method further includes receiving the genomic data selection function from a sender. The sender can be the entity to whom the genomic data belongs or someone who is acting on behalf of the entity to whom the genomic data belongs.

In at least one implementation, the genomic data can include one of transcriptome sequence data, RNA sequence data, DNA or RNA base modification data, DNA methylation data, DNA acetylation data, bisulfite sequencing data, chromatin data, chromatin immunoprecipitation data, chromatin immunoprecipitation sequencing data, DNAase digestion data, or nucleic acid secondary structure data. In yet another implementation, the genomic data includes at least one of a phenotype information, a medical record, a drug safety data, drug efficacy data, disease risk information, health risk information, medical prognosis information, probable outcomes information, therapeutic recommendations, medical interventions recommendations, behavior information, nutrition habit information, dietary habit information, environmental exposure information, environmental condition information, personal attribute data, sample attribute data.

Figure 3:
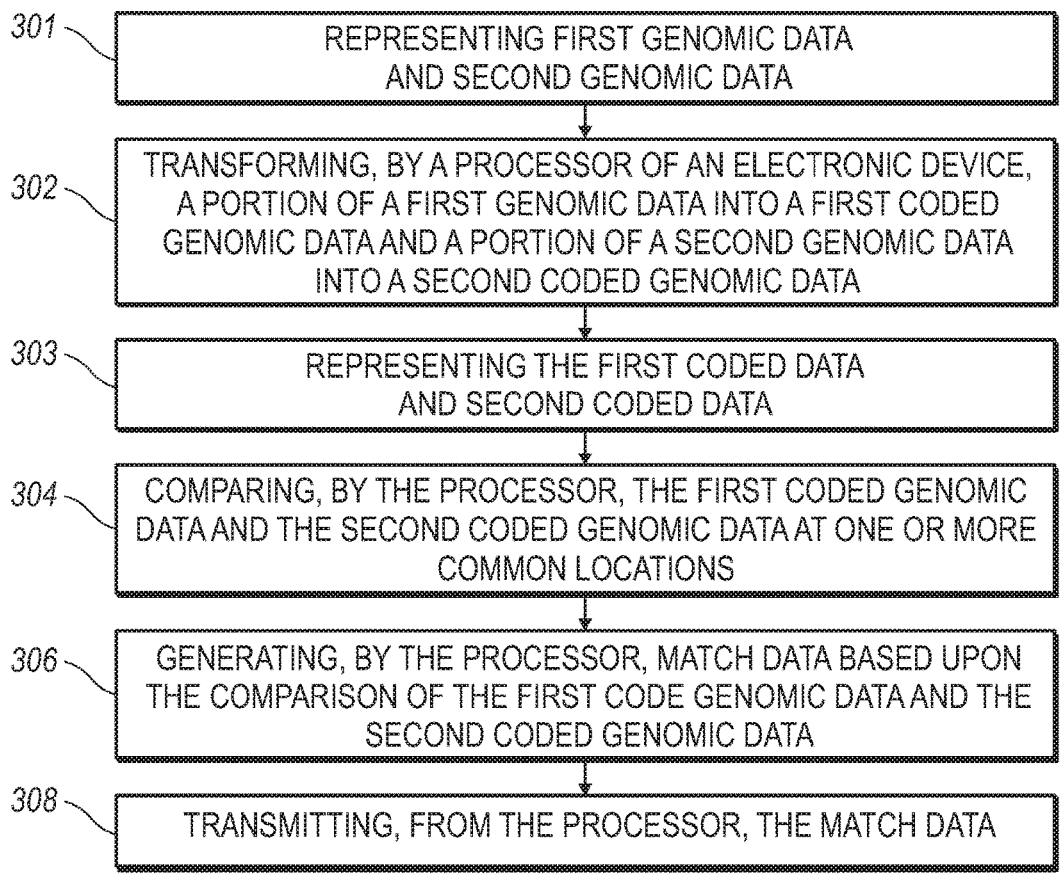
FIG. 3 is flow chart illustrating a comparison scheme according to an example implementation.

FIG. 3 presents a method 300 for comparing genomic data on an electronic device. The method 300 can include one or more of the steps as presented in FIG. 3. Furthermore, the method 300 can include additional steps which are not illustrated. While the method 300 is arranged in a particular order, the order of the steps can be different in other embodiments.

The method 300 can include transforming, by a processor of an electronic device, a portion of a first genomic data into a first coded genomic data and a portion of a second genomic data into a second coded genomic data (302). Optionally, as indicated at block 301, the method can further include representing first genomic data and second genomic data. The first genomic data can be received from a first source. The second genomic data can be received from a second source. The first source can be an entity such as a human or other animal. In yet other embodiments, the entity can be any organism that has genomic data. Likewise, the second source can be an entity such as a human or other animal. In yet other embodiments, the entity can be any organism that has genomic data. The first and second source can be a further processed source such as a memory of an electronic device, output from an electronic device or other similar source.

In at least one embodiment, the transforming of the first genomic data can further include applying a cryptographic hash function to the first genomic data (302). Additionally, the transforming of the second genomic data can include applying a cryptographic hash function to the second genomic data. An implementation of the system and methods incorporating application of a cryptographic hash function to genomic DNA sequence information can typically transform a plaintext genomic sequence of arbitrary length (e.g., ACGTTGCA) into a fixed length alphanumeric bit string (e.g. 35b667b7dbc45bee23aa71842b9068db).

The method of transforming genomic data input with a cryptographic hash function can further include simultaneously compressing input plaintext sequence information. Implementation incorporating MD5 as a cryptographic hash function can take an arbitrarily long genome sequence (e.g., >>128 bits) and transform that sequence into a 128 bit string.

The method of transforming genomic sequence input with a cryptographic hash function can further produce an avalanche effect, whereby very small changes on otherwise identical genomic data input can result in dramatically different coded genomic data output. For example, the representation of the first genomic data and the second genomic data (301) if slightly changed can result in a widely different representation of the first coded data and the second coded data (303). Conversely the method can transform identical genome sequence or genomic data (301) inputs, generating identical coded genomic data (303) or hash digest output using a cryptographic hash function.

Thus, the method can further provide genomic data security and can prevent recovering the original input genomic data input when given only the genomic data hash digest or coded genomic data output—it is impractical given current computational technology to invert the cryptographic hash function to reverse transform the coded genomic data (303) to produce the original genomic data (301).

In at least one embodiment, the transforming the portion of the first genomic data and the portion of the second genomic data can occur by operation of a hybrid key encryption protocol. In yet another embodiment, transforming the portion of the first genomic data and the portion of the second genomic data can invoke application of an asymmetric key encryption protocol. In still another implementation, the transforming the portion of the first genomic data and the portion of the second genomic data can occurs by application of a symmetric key encryption protocol.

More complex measures of the similarity of two genomic data can be mathematically intractable for genomic data transformed with typical cryptographic hash functions. If the two genomic data, such as two genome sequences, represent identical genomic data input (301), then the two cryptographic hash digest outputs, or coded genomic data (303) will match, otherwise the cryptographic hash output will differ even when the overall sequences are similar or only differ by as few as one DNA base at only one sequence position in a long string of genome sequence data.

The described possible embodiment can further enable two or more individuals use an electronic device to transform their genomic data into encoded form, and can shield their underlying genomic data from disclosure while protecting the anonymity of the source as well.

In one possible implementation two or more persons or entities can share encoded genomic data (303), the system of method can further include using their electronic devices to compare their (first) encoded genomic data to the other's (second) encoded genomic data.

In yet another embodiment of the system, the transforming the first genomic data can further include applying a homomorphic encryption function to the first genomic data (302). In yet another embodiment, the transforming the second genomic data includes applying a homomorphic encryption function to the second genomic data.

In at least one embodiment, the transformation of the first genomic data is the same as the transformation of the second genomic data. For example, if the first genomic data is transformed using a homomorphic encryption function, the second genomic data is transformed using a homomorphic encryption function. Furthermore, in at least one implementation, when a homomorphic encryption function is implemented, the same homomorphic encryption function is used. In yet other embodiments, a different homomorphic encryption function can be implemented. Additionally, in other embodiments, the first genomic data can be transformed using a cryptographic has function and the second genomic data can be transformed using a homomorphic encryption function or vice versa. In yet other embodiments, other transformations are considered within the scope of this disclosure.

The implementation of the system or method incorporating transforming the genomic data by homomorphic encryption of genomic data (302) can further offer important advantages for comparing and measuring the similarities or differences among genomic data.

In at least one embodiment, the wherein transforming the second genomic data includes applying a homomorphic encryption function to the second genomic data. This system implementation wherein the at least a first and second genomic data are transformed by homomorphic encryption (302) can enable a spectrum of novel applications (302).

The method can further involve transforming genome sequence data from two individuals using homomorphic encryption functions.

The method of homomorphically transforming genomic data (302) can further involve comparing and scoring matches for similarities in addition to exact matches.

The method can further include many more comparisons and much more complex evaluations of similarity than simple exact matches at all sequence positions evaluated, included but not limited to homology evaluations, sequence alignments, identification of sequence variants and other sophisticated analyses.

Furthermore, and importantly for many possible implementations and embodiments of the system, homomorphic encryption can enable a non-trusted third party to conduct the encoded genomic data processing, including but not limited to encoded genomic data comparison operations, and encoded genomic data matching evaluations, without risk that the underlying genomic data will be revealed, or the identities or the genomic health and ancestry or other genomic information of the individuals or samples represented by the underlying genomic data compromised.

In at least one embodiment, the first genomic data is unencrypted data or encrypted data. In at least one embodiment, the second genomic data is unencrypted data or encrypted data.

In at least one embodiment, the portion of the first genomic data is one or more predetermined loci of the first genomic data. The predetermined loci can be based upon a requested comparison. The requested comparison can be a measure of the number of matching loci. The requested comparison can be a measure of the length of a predetermined number strings of nucleic acid bases of the first genomic data substantially matching a predetermined number strings of nucleic acid bases of the second genomic data. The requested comparison can be a measure of the length of a predetermined number strings of genome sequences of the first genomic data substantially matching a predetermined number strings of genome sequences of the second genomic data. The requested comparison can be a percent identity of the number loci of the predetermined portion of the first genomic data substantially matching the loci of the predetermined portion of the second genomic data.

In at least one embodiment, the requested transformation can be a one-way cryptographic hash function. In yet another embodiment, the requested transformation can be obtained by application of a garbled circuit algorithm. In still another embodiment, the requested transformation can be obtained by application of a zero-knowledge protocol.

In at least one implementation, the determination of the one or more predetermined loci constituting the portion of the first genomic data can be obtained by application of a selection function. In at least one embodiment, the selection function specifies at least a part of the portion of the first genomic data known or suspected to be hypervariable or probably most discriminative of genomic data derived from two related but distinct samples or individuals. Additionally, the determination of the one or more loci or one or more sequences constituting the portion of the second genomic data can be obtained by application of the function or protocol used to determine the one or more loci or one or more sequences constituting the portion of the first genomic data.

The method 300 can further include comparing, by the processor, the first coded genomic data and the second coded genomic data at one or more common locations (304). The method can further allow selected encoded genomic data from one individual to be represented and quickly compared with encoded genomic data from equivalent regions from other genomes (304). The method implementing transforming by operation of homomorphic encryption (302) can further enable more complex genomic data comparing operations (304), including but not limited to searching for non-exact genomic data matches; for instance, the system or method transforming with a homomorphic encryption function can enable comparing genome sequences merely similar or homologous to another sequence (304), as well as exact matches.

In at least one implementation, the comparing can involve oblivious sorting of the first encoded genomic data by genomic position or coordinate information using a fixed sequence of comparisons, and independently sorting the second encoded genomic data according to the same scheme of a fixed sequence of comparisons, and then subsequently, merging the sorted first encoded genomic data with the sorted second encoded genomic data by applying a bitonic merger protocol to generate a sorted union of their encoded genomic data. The method can further include one or more of the following: comparing the adjacent elements of the merged, sorted genomic data using a garbled circuit protocol; and generating a list or set of matching genomic data elements comprising match data by application of a duplication select protocol to the adjacent elements of the merged genomic data. The method can further include shuffling the match data prior to transmitting the match data.

The method 300 can further include generating, by the processor, match data based upon the comparison of the first coded genomic data and the second coded genomic data (306). In another embodiment, the method can further include generating by a processor, match data, which can include scoring and tabulating instances of exact matches between the first coded and second coded genomic data. In yet other embodiments, the method can include both of the above described generating steps.

Various system implementations and embodiments, including but not limited to system implementations or embodiments transforming genomic data with cryptographic hash functions, can enable applications that can allow individuals, entities or groups to share genomic data, compare the similarity of genomic data (304), calculate the percent identical genomic data (306), and determine the relatedness or return other measures of the evolutionary or genetic relationship among two or more samples or individuals. However, the system's ability to compare and measure the differences between genome sequences after they have been transformed by application of cryptographic hash function can remain limited to scoring a match or no match (306) if the transforming operation is the output of a cryptographic hash function. The system or method can further enable either person or entity to score and record the encoded genomic data matches (306). The present method can enable new comparing (304) and matching (306) capabilities—including but not limited to comparing (304) and generating homology data or non-exact matching of encrypted genomic data (306).

The method 300 can further include transmitting, from the processor, the match data (308). The system or method can further include either or both person or entity to transmit the match data to output (308) where it can be viewed, interpreted and used by the other person or entity, or a third party.

Figure 4:
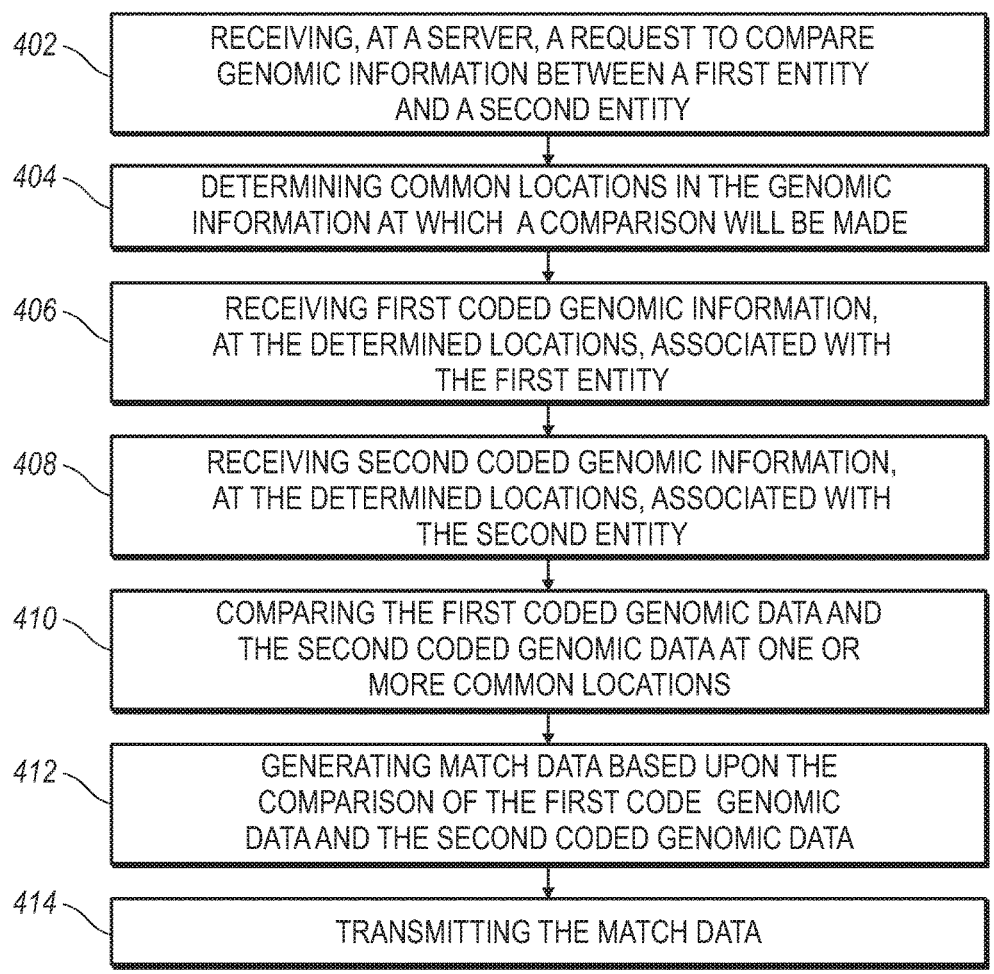
FIG. 4 is flow chart illustrating a comparison scheme according to another example implementation.

FIG. 4 presents a method 400 for comparing genomic data on an electronic device. The method 400 can include one or more of the steps as presented in FIG. 4. Furthermore, the method 400 can include additional steps which are not illustrated. While the method 400 is arranged in a particular order, the order of the steps can be different in other embodiments.

The method 400 can include receiving, at a server, a request to compare genomic information associated with a first entity with genomic information associated with a second entity (402).

The method 400 can further include determining common locations in the genomic information at which comparisons will be made (404).

The method 400 can further include receiving first coded genomic information, at the determined locations, associated with the first entity in response to a request for the first coded genomic information (406).

The method 400 can further include receiving second coded genomic information, at the determined locations, associated with the second entity in response to a request for the second coded genomic information (408).

The method 400 can further include comparing the first coded genomic data and the second coded genomic data at one or more determined common locations (410).

The method 400 can further include generating match data based upon the comparison of the first coded genomic data and the second coded genomic data (412).

The method 400 can further include transmitting the match data (414).

Figure 5:
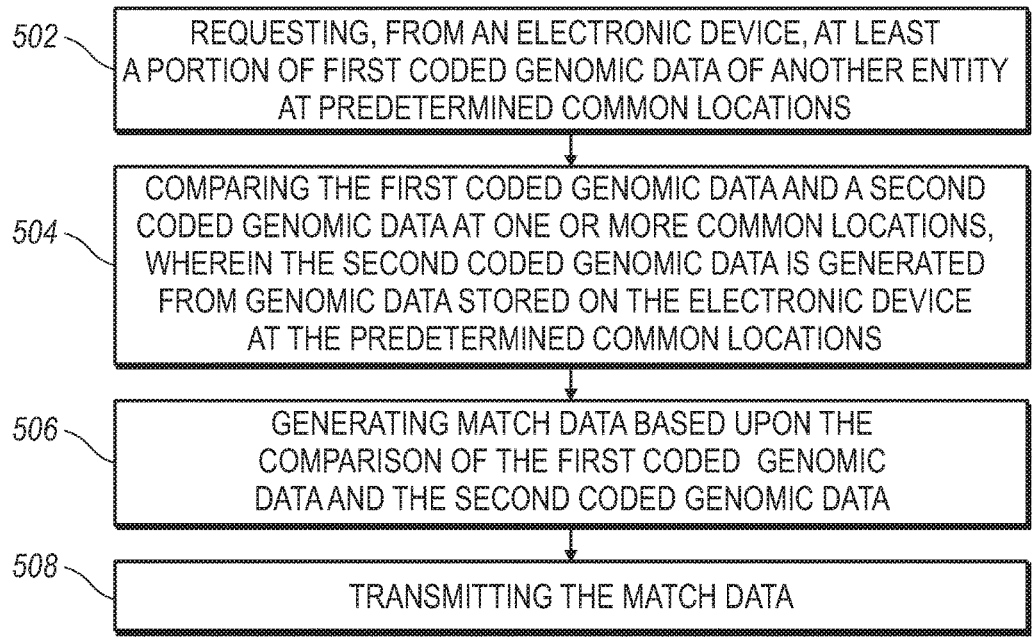
FIG. 5 is flow chart illustrating a comparison scheme according to yet another example implementation.

FIG. 5 presents a method 500 for comparing genomic data on an electronic device. The method 500 can include one or more of the steps as presented in FIG. 5. Furthermore, the method 500 can include additional steps which are not illustrated. While the method 500 is arranged in a particular order, the order of the steps can be different in other embodiments.

The method 500 can include requesting, from an electronic device, at least a portion of first coded genomic data of another entity at predetermined common locations (502).

The method 500 can further comparing the first coded genomic data and a second coded genomic data at one or more common locations, wherein the second coded genomic data is generated from genomic data stored on the electronic device at the predetermined locations (504).

The method 500 can further include generating match data based upon the comparison of the first code genomic data and the second coded genomic data (506).

The method 500 can further include transmitting the match data (508).

Figure 6:
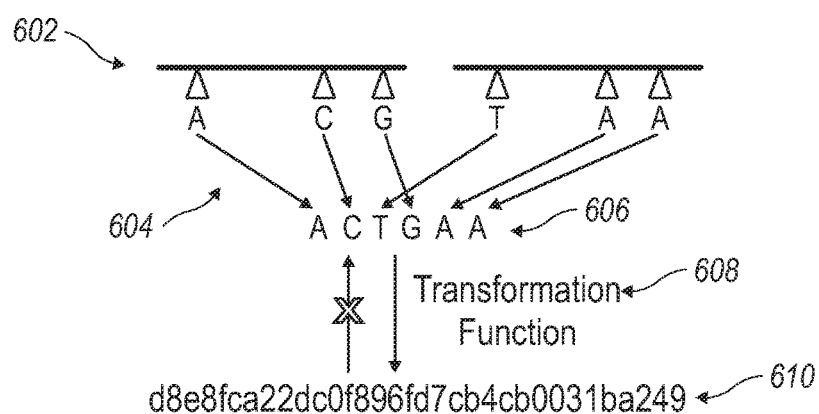
FIG. 6 illustrates a diagrammatic illustration of a transformation function being applied to loci of genome according to an example implementation.

FIG. 6 is a diagrammatic illustration of one possible embodiment of the system, the embodiment including selecting a portion of the genomic data, which can be but is not limited to dividing the genome into blocks (lines in 602), and from among the blocks selecting the loci to be evaluated.

FIG. 6 further illustrates that the data selecting can be accomplished by operation of a function, or data can be predetermined according to the requested comparison (A,C, G,T,A,A in 602).

The illustrated embodiment can further include dividing the genomic data into one or more blocks or loci (602).

The illustrated embodiment depicts that the blocks or loci can be further permuted or shuffled according to a function or selection operation (604).

The illustrated embodiment can further include selecting, wherein selecting the portion of the genomic data can be by means of operation of a function on the genomic data blocks (604) to yield the portion of the genomic data to be transformed (606).

The illustration further illustrates that one possible embodiment can be transforming the genomic data by operation of cryptographic hash function (608).

FIG. 6 illustrates that transforming by application of a cryptographic hash function can produce a fixed length encrypted portion of genomic data according to the illustrated example (610). Genomic data from selected regions of the genome are transformed for uses including comparison with genomic data from other genomes. In this example, the genomic data are transformed using one-way cryptographic hash, yielding a coded representation of the genomic data that can be used for comparison with other genomes, but which is computationally impractical to use for determining the original genomic data.

Figure 7A:
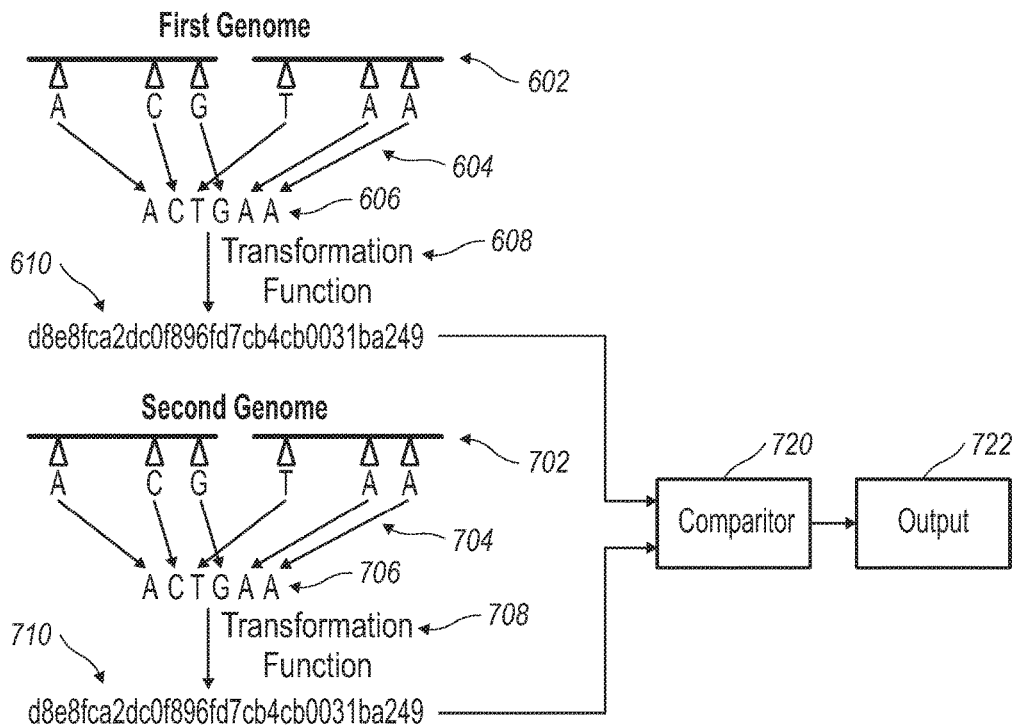
FIG. 7A illustrates a diagrammatic illustration of a comparison of a first and second genome after a transformation function has been applied via a comparator according to an example implementation.

FIG. 7A provides a diagrammatic illustration of one possible embodiment of a comparison of a first (610) and second genome after a transformation function has been applied (710). The comparing can occur via a comparator embodied in a processor or electronic device according to an example implementation. In this example the selected, shuffled portions of the first genome (606) and the selected, shuffled portions of the second genome (706) are transformed (608, 708), the transformed representations of the genomic data (610, 710) are compared (720), and determined to be identical at the regions tested (720).

Figure 7B:
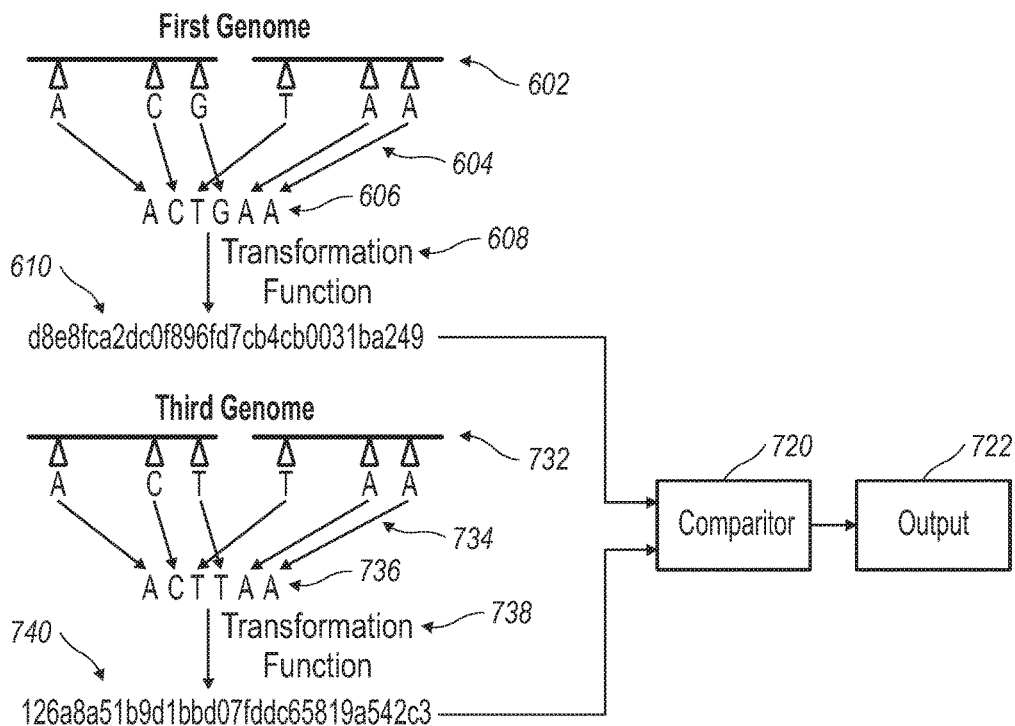
FIG. 7B illustrates a diagrammatic illustration of a comparison of a first and third genome after a transformation function has been applied via a comparator according to an example implementation.

FIG. 7B depicts a diagrammatic illustration of a comparison of a first and third genome after a transformation function has been applied via a comparator according to an example implementation. In the depicted example portions of the genomic data of the first genome and the third genome are divided into blocks (lines in 602 and lines in 732), genomic loci are selected and shuffled (604, 734), yielding a portion of the first and third genomic data (606, 736). The depicted embodiment transforms the respective portions of genomic data by application of a cryptographic hash function, producing the transformed representations of the genomic data (610, 740), that can be compared (720), and determined not identical (no match) at the tested loci.

Figure 8A:
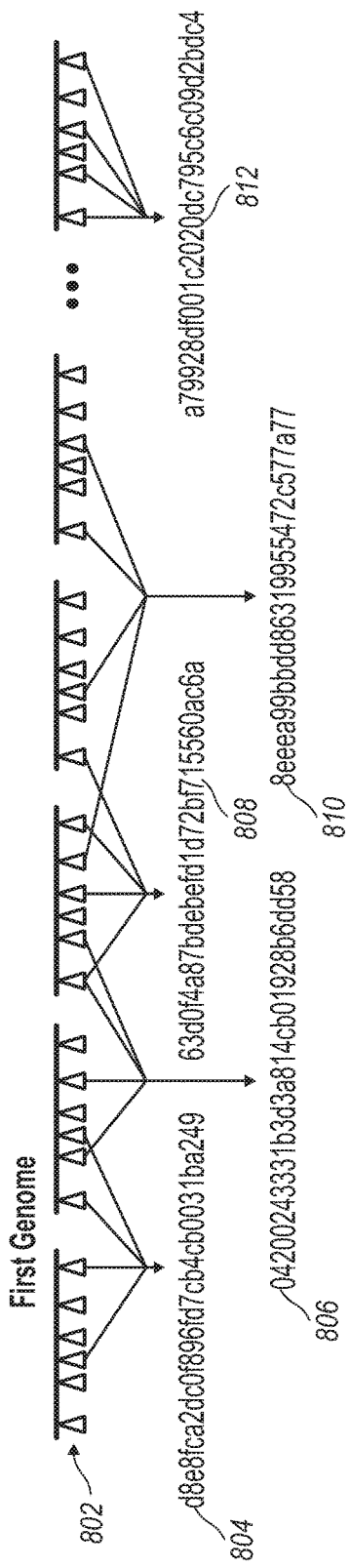
FIG. 8A illustrates a diagrammatic transformation of a first genome into encoded data according to an example implementation.

FIG. 8A illustrates a diagrammatic representation of an implementation of the system operating on multiple portions of a first and fourth genomic data, limited only by the particular illustration, which illustration is not an exhaustive or fully elaborative illustration of all possible embodiments of various implementations of the system. The implementation depicted includes dividing the first and second genomic data into blocks of corresponding sequence or genomic data features (lines in 802 of FIG. 8A, and 832 of FIG. 8B), selecting and shuffling portions of the genomic data contained in the various data blocks according to a function or predetermined specification of the loci to be compared, and the selected, shuffled portions of genomic data transformed by application of a cryptographic hash function into fixed length alphanumeric bit strings (e.g., 804, 806, 808, 810 and 812 of a first genomic data; 834, 836, 838, 849 and 842 of a fourth genomic data) This such transformation performed on several sets of loci in the genome yields a set of transformed genomic data that can be compared with the corresponding transformed genomic data from the same region in other genomes, and matching genomic data recorded (e.g. 804=834, 806=836, 808=838, 810=840, but 812 does not equal 842; 4 out of 5 regions match; genomes are 80% identical at compared loci) to yield a measure of the similarity of the two genomes, as shown for example in FIG. 9.

Figure 8B:
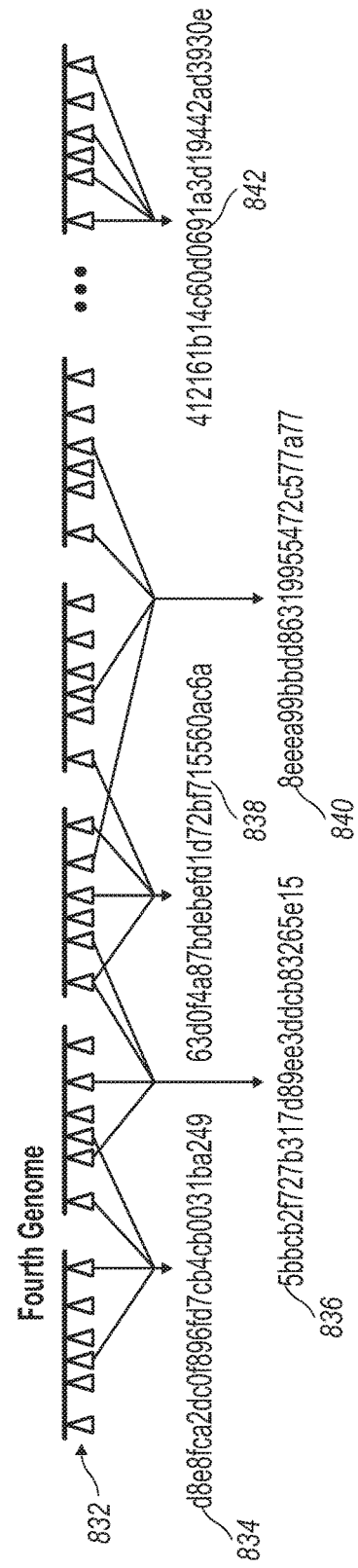
FIG. 8B illustrates a diagrammatic transformation of a fourth genome into encoded data according to an example implementation.

FIG. 8B illustrates a diagrammatic transformation of a fourth genome into encoded data according to an example implementation.

Figure 8C:
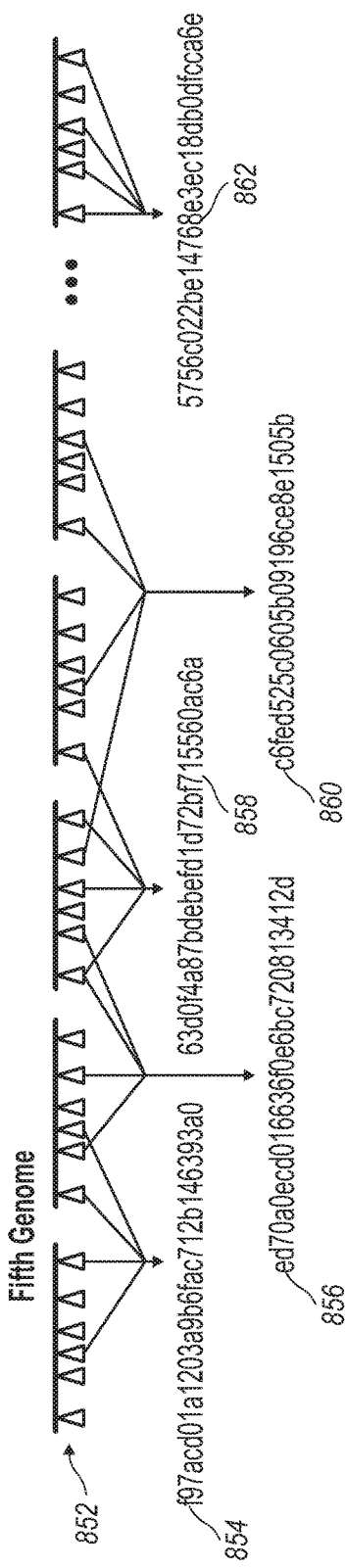
FIG. 8C illustrates a diagrammatic transformation of a fifth genome into encoded data according to an example implementation.

FIG. 8C illustrates a diagrammatic transformation of a fifth genome into encoded data according to an example implementation.

Figure 8D:
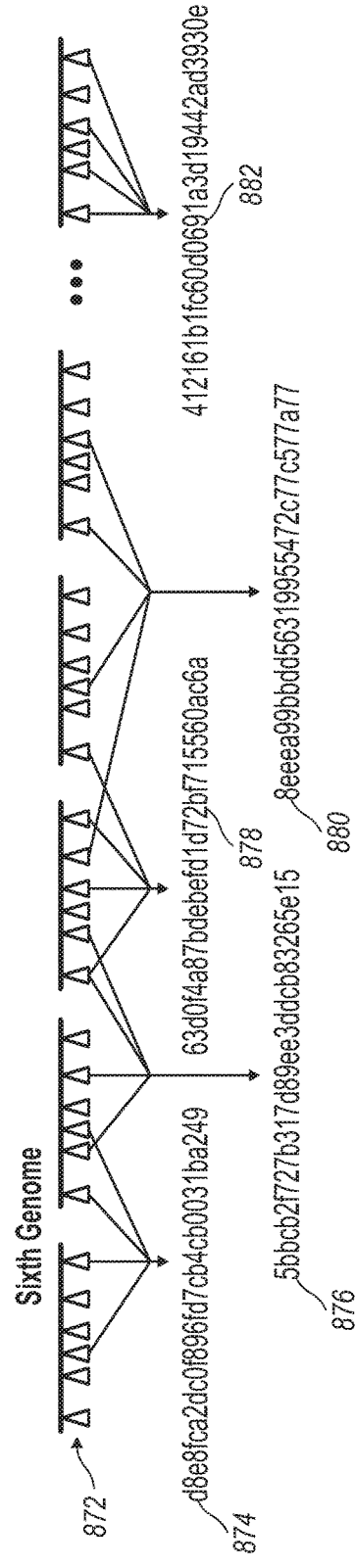
FIG. 8D illustrates a diagrammatic transformation of a sixth genome into encoded data according to an example implementation.

FIG. 8D illustrates a diagrammatic transformation of a sixth genome into encoded data according to an example implementation.

Figure 9:
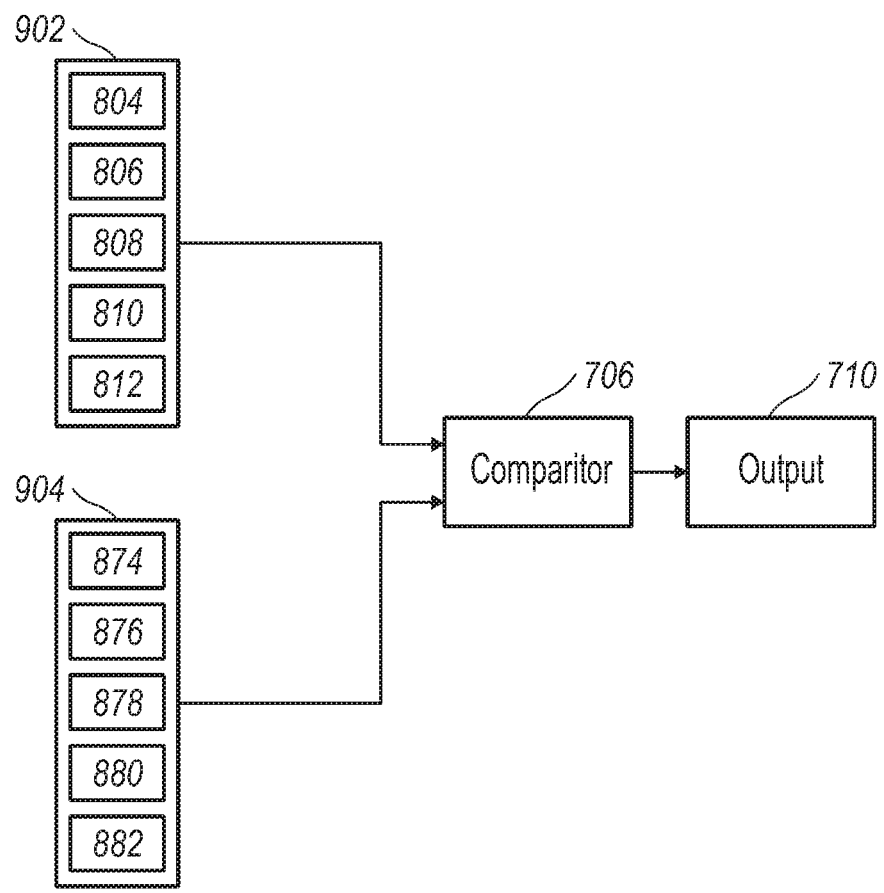
FIG. 9 illustrates a diagrammatic comparison of a first set of encoded genomic data with a second set of encoded genomic data according to an example implementation.

FIG. 9 illustrates a diagrammatic comparison of a first set of encoded genomic data with a second set of encoded genomic data according to an example implementation. The illustrated example implementation compares a portion of a first encoded genomic data (804, 806, 808, 810, 812) with a portion of a sixth encoded genomic data (874, 876, 878, 880, 892). The comparing of the corresponding encoded genomic data features by a processor, including a processor operating in an electronic device, records matching genomic loci, and as in the illustration can produce match data, illustrated by the cryptographic hash function output identities of (804/874=1; 806/876=0; 808/878=1; 810/880=1; 812/882=0)

Figure 10:
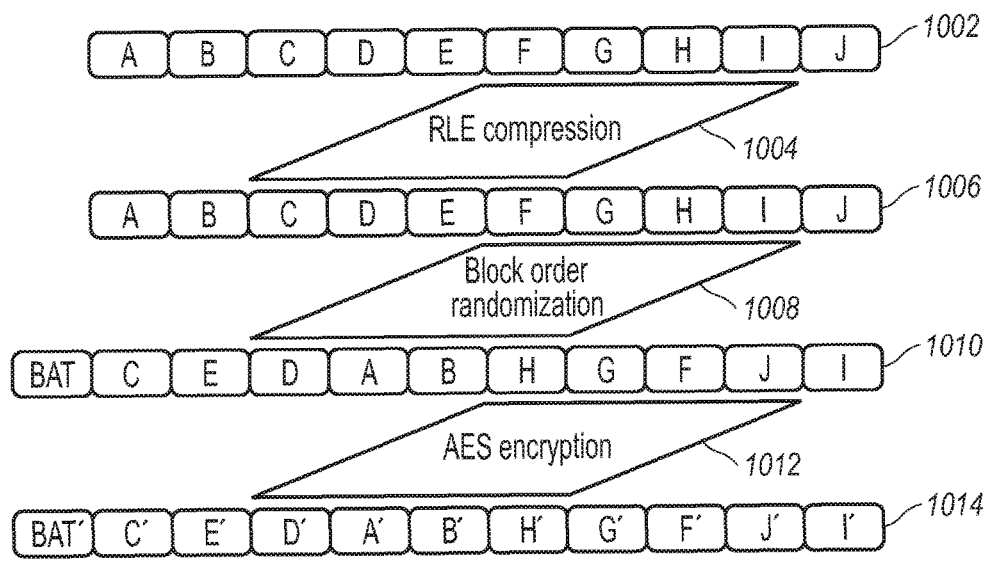
FIG. 10 illustrates an example of an encryption scheme for genomic data according to an example implementation.

FIG. 10 illustrates an example of an encryption scheme for genomic data according to an example implementation.

FIG. 10 illustrates a diagrammatic division of a portion of the genomic data into genomic data blocks (1002)

FIG. 10 further illustrates compressing the genomic data with run length encoding (1004) to yield compressed genomic data blocks (1006).

FIG. 10 further illustrates the shuffling of genomic data blocks into one of a random order of genomic data blocks (1008), with mapping or indexing of genomic data block order or content data stored in a separate genomic data block, illustrated in the diagrammatic representation as a block allocation table (BAT in 1010).

FIG. 10 further depicts the encrypting of genomic data blocks using but one of many possible encryption schemes, illustrated in this example of one possible implementation by application of the AES encryption protocol (1012).

FIG. 10 further depicts an example of an encryption scheme for genomic data generating as output a compressed, shuffled, encoded genomic data (1014).

As indicated above, the technology can be implemented on one or more electronic devices. The electronic devices can be a server, a computer, a laptop, a desktop, a tablet, a smartphone, a handheld device, a personal data assistant, or the other device which includes one or more processors. The electronic device can further include memory, which can be non-transitory memory. Examples within the scope of the present disclosure may also include tangible and/or non-transitory computer-readable storage media for carrying or having computer-executable instructions or data structures stored thereon. Such non-transitory computer-readable storage media can be any available media that can be accessed by a general purpose or special purpose computer, including the functional design of any special purpose processor as discussed above. By way of example, and not limitation, such non-transitory computer-readable media can include RAM, ROM, EEPROM, CD-ROM or other optical disk storage, magnetic disk storage or other magnetic storage devices, or any other medium which can be used to carry or store desired program code means in the form of computer-executable instructions, data structures, or processor chip design. When information is transferred or provided over a network or another communications connection (either hardwired, wireless, or combination thereof) to a computer, the computer properly views the connection as a computer-readable medium. Thus, any such connection is properly termed a computer-readable medium. Combinations of the above should also be included within the scope of the computer-readable media.

Computer-executable instructions include, for example, instructions and data which cause a general purpose computer, special purpose computer, or special purpose processing device to perform a certain function or group of functions. Computer-executable instructions also include program modules that are executed by computers in stand-alone or network environments. Generally, program modules include routines, programs, components, data structures, objects, and the functions inherent in the design of special-purpose processors, etc. that perform particular tasks or implement particular abstract data types. Computer-executable instructions, associated data structures, and program modules represent examples of the program code means for executing steps of the methods disclosed herein. The particular sequence of such executable instructions or associated data structures represents examples of corresponding acts for implementing the functions described in such steps.

Those of skill in the art will appreciate that other examples of the disclosure may be practiced in network computing environments with many types of computer system configurations, including personal computers, hand-held devices, multi-processor systems, microprocessor-based or programmable consumer electronics, network PCs, minicomputers, mainframe computers, and the like. Examples may also be practiced in distributed computing environments where tasks are performed by local and remote processing devices that are linked (either by hardwired links, wireless links, or by a combination thereof) through a communications network. In a distributed computing environment, program modules may be located in both local and remote memory storage devices.

Figure 11:
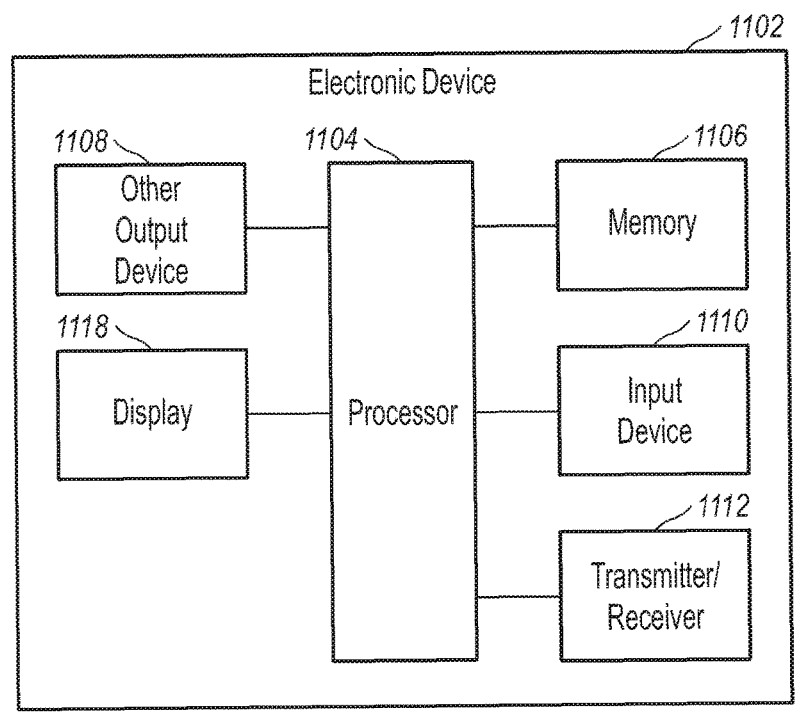
FIG. 11 illustrates an example of an electronic device according to an example implementation.

FIG. 11 illustrates an example of an electronic device 1102 according to an example implementation. As illustrated, the electronic device includes a processor 1104. The processor can be communicatively coupled to one or more of the components of the electronic device 1102. For example, the processor is communicatively coupled to memory 1106. The memory 1106 can be RAM, ROM, flash or any other type of memory including transitory and non-transitory memory. The processor 1104 can be communicatively coupled to an input device 1110 that is configured to enable an operator to input data to the electronic device 1102. The input device can be a keyboard, touchscreen, navigation tool or other device that is configured to provide data to the electronic device 1102 for data input. The processor 1104 can be further communicatively coupled to a transmitter/receiver 1112. The transmitter/receiver 1112 can include one or more transmitters/receivers. The transmitters enable the device to transmit data externally to the device, and the receivers enable the device to receive data from a source external to the device. In at least one embodiment, the transmitter/receiver can be a single device and in other embodiments, they can be separate devices. The processor 1104 can further be communicatively coupled to a display 1118 for displaying of data to an operator. Furthermore, the processor 1104 can further be coupled to at least one other output device 1108. These are other devices which enable the electronic device 1102 to output data to an operator.

The electronic device 1102 can be anyone of the above described devices. In some embodiments, the electronic device 1102 can include only some of the components illustrated in FIG. 11. Additionally, the electronic device 1102 can include additional components which are not illustrated.

The electronic device 1102 can be configured such that the processor 1104 is capable and/or configured to execute the steps as recited in the methods presented herein. The memory 1106 is configured to store the data. Furthermore, the transmitter 1112 is configured to transmit data from the electronic device 1102.

Figure 12:
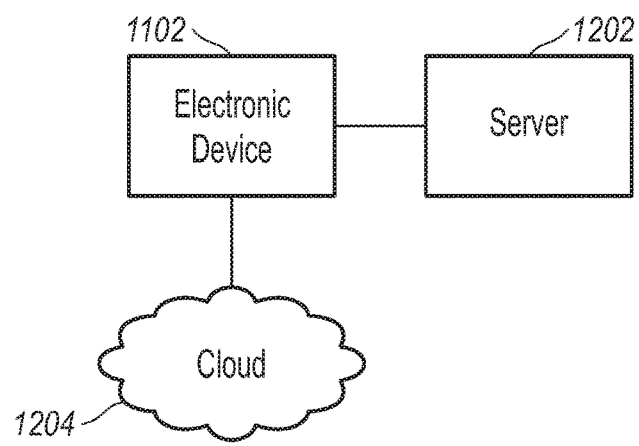
FIG. 12 illustrates the example electronic device in communication with a cloud and a server according to an example implementation in order to make a comparison of encoded data according to the present technology.

FIG. 12 illustrates the example electronic device 1102 in communication with a cloud 1204 and a server 1202 according to an example implementation in order to make a comparison of encoded data according to the present technology. The system 1200 enables the executing of the steps of the methods as described above on one or more of the server 1202, electronic device 1102, and the cloud 1204. Portions of the method can be executed on the respective component as necessary.

Figure 13:
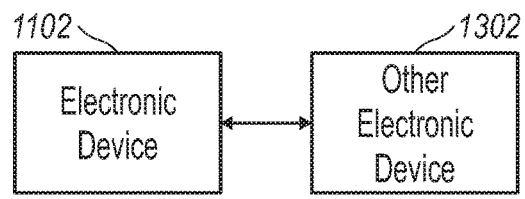
FIG. 13 illustrates an example of a peer-to-peer coupling of an electronic device and another electronic device in order to make a comparison of encoded data according to the present technology.

FIG. 13 illustrates an example of a peer-to-peer coupling of an electronic device 1102 and another electronic device 1302 in order to make a comparison of encoded data according to the present technology. The peer-to-peer coupling allows for the sharing of genomic data between the electronic device 1102 and the another electronic device 1302 so that an operator of the electronic device can receive genomic data (in at least one embodiment, encoded or encrypted genomic data) from the another electronic device 1302 so that a comparison of the genomic data can be performed according to any of the above described methods. Furthermore, the another electronic device 1302 can send encrypted data to the electronic device 1102, according to the methods presented herein. Likewise, the electronic device 1102 can send encrypted data to the another electronic device 1302.

Figure 14:
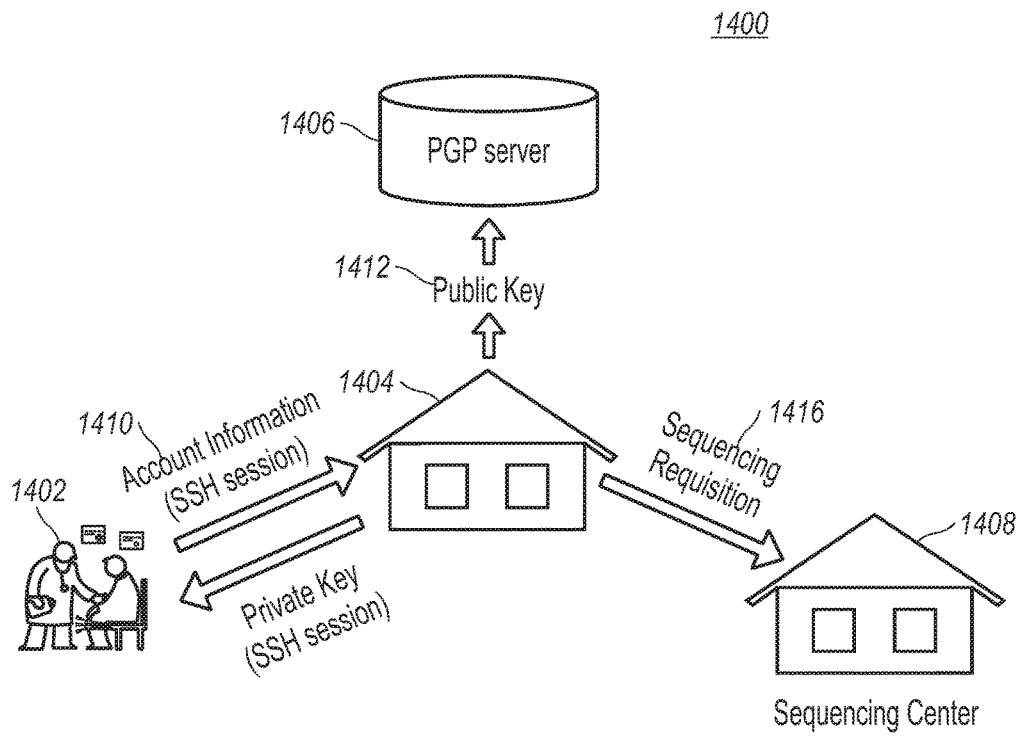
FIG. 14 illustrates a system of sharing encoded data according to an example implementation.

FIG. 14 illustrates a system of sharing encoded data according to an example implementation. The system can include a patient or health care provider (1402), FIG. 14 further illustrates that the patient or healthcare provider can requisition the provision of services by an intermediary (1404).

FIG. 14 further illustrates that in at least one embodiment the services can include the negotiation of a secure data transmission protocol (1410), FIG. 14 illustrates that the system can further include the generation of a public and private key pair specific to the healthcare provider and/or the patient (1410) (1412).

FIG. 14 further illustrates that the system can further include the transmission of the private key back to the patient or healthcare provider (1410), and the posting of the public key to a key server (1406).

FIG. 14 further illustrates that in at least one embodiment of the system, the intermediary can associate the public key data with at least one sample identification data (1412) that can obscure the identity of the patient, the healthcare provider and association of the sample with the patient's personally identifiable information, including but not limited to the patient's genomic data.

FIG. 14 further illustrates that the intermediary (1404) can function in variety of roles, including but not limited to serving as an entity that can receive a sample from the healthcare provider or patient (1402), and pass the sequencing requisition on to a sequencing center (1408), where the patient's data will be sequenced.

Figure 15:
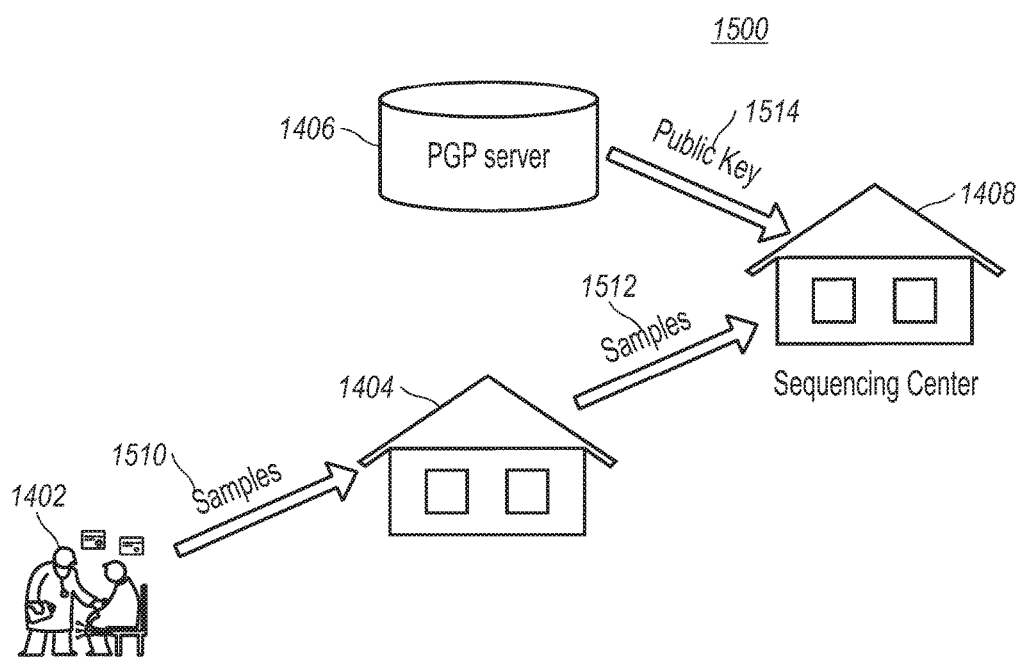
FIG. 15 illustrates another system of sharing encoded data according to an example implementation.

FIG. 15 illustrates another aspect of the system, specifically that the system can pass the patient's sample (1510) to the intermediary (1404).

FIG. 15 further illustrates that the system can operate to allow the intermediary to hide the identity of the patient or healthcare provider, but pass on the sample to the sequencing center after obscuring the identity of the patient or sample or associating an anonymous identification data with the sample (1512), thus providing patient anonymity and security for the genomic data generated from the sample (1510).

FIG. 15 further illustrates that in at least one embodiment of the system, the intermediary may associate a unique identification data with the sample, and pass the sample and the at least one unique identification data (1512) to the sequencing center (1408).

FIG. 15 further illustrates that the system can use the public key (1514) associated with the at least one unique identification data to encrypt the genomic data generated by the sequencing center (1408) from the sample associated with the at least one unique identification data (1512).

Figure 16:
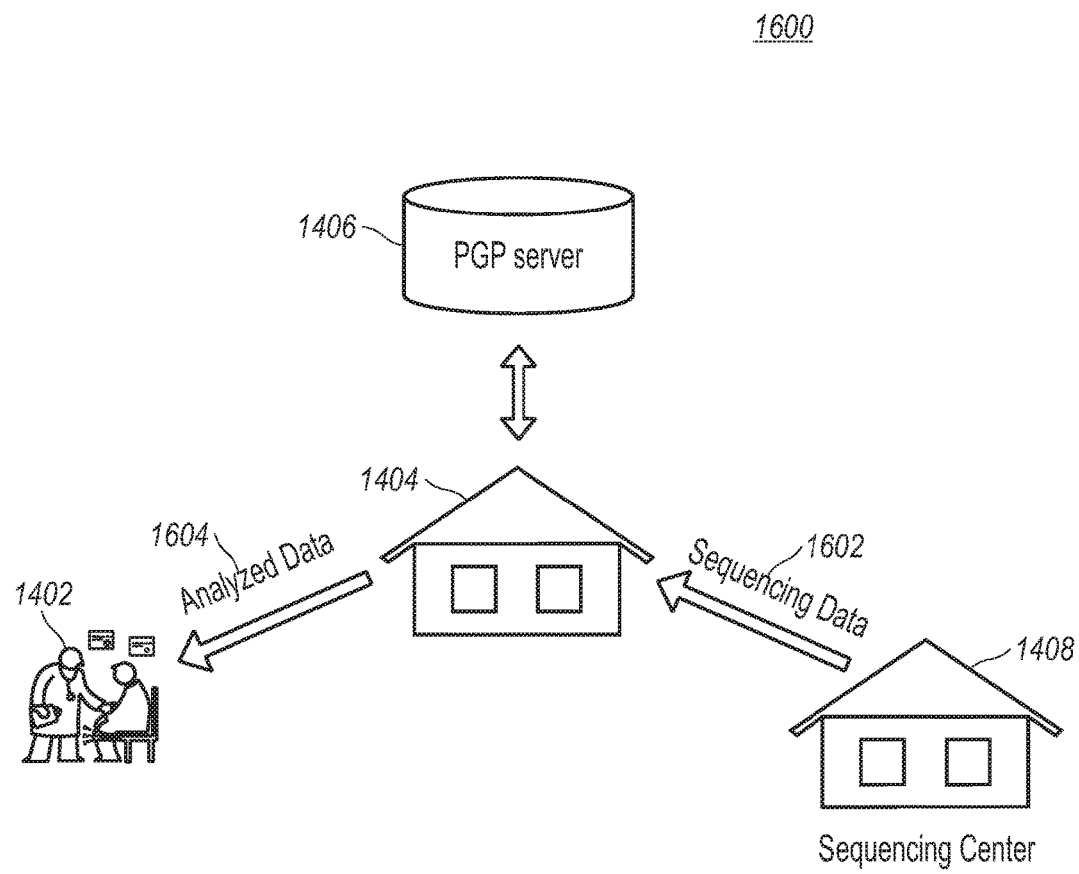
FIG. 16 illustrates a system of decoding encoded data according to an example implementation.

FIG. 16 illustrates a system of analyzing and decoding encoded genomic data according to an example implementation.

FIG. 16 further illustrates that the sequencing center (1408) can send the encrypted data (1602) back to the intermediary (1404) for processing.

FIG. 16 further illustrates that in at least one embodiment of the system the intermediary (1404) may use the at least one unique identification data associated with the sequencing data (1602) to obtain the private key from storage, and decrypt at least a portion of the encoded genomic data to enable processing and data analysis, FIG. 16 further illustrates that in at least one embodiment of the system the intermediary can use the public key obtained from the PGP server (1406) to re-encrypt the analyzed genomic data and transmit (1604) the encoded, analyzed data back to the patient or healthcare provider (1402).

The various embodiments described above are provided by way of illustration only and should not be construed to limit the scope of the disclosure. Those skilled in the art will readily recognize various modifications and changes that may be made to the principles described herein without following the example embodiments and applications illustrated and described herein, and without departing from the scope of the disclosure.

What is claimed is:

1. A method for comparing genome data comprising:
generating, by a processor of an electronic device, first unique identification data associated with at least a portion of a first genome and second unique identification data associated with at least a portion of a second genome;
generating a first encryption key associated with the first genome and a second encryption key associated with the second genome;
indexing the first encryption key using the first unique identification data and the second encryption key using the second unique identification data;
selecting at least part of the first genome and the second genome;
encrypting at least part of the first genome into first coded genomic data using the first encryption key and at least part of the second genome into second coded genomic data using the second encryption key;
indexing the first coded genomic data using the first unique identification data and the second coded genomic data using the second unique identification data;
storing the first coded genomic data and second coded genomic data on the electronic device;
dividing at least a portion of the first coded genomic data and second coded genomic data into blocks;

generating first genomic block data and second genomic block data in response to indexing at least part of the first coded genomic data and second coded genomic data, respectively, in a data block by a genomic coordinate, an order, or genomic data content information;

storing at least part of the first genomic block data and at least part of the second genomic block data in a corresponding genome block allocation table;

comparing, by the processor: (i) the first genome and the second genome, or the first coded genomic data and the second coded genomic data, or the first genomic block data and second genomic block data; or, (ii) first coded or uncoded genomic data and second coded or uncoded genomic data associated with phenotype, genotype, trait, disease, drug response, medical condition or behavior;

generating, by the processor, match data based upon the comparison; and storing, from the processor, the match data, indexed by the first unique identification data and the second unique identification data.

2. The method as recited in claim 1, wherein the encrypting includes applying a cryptographic hash function or a homomorphic encryption function that allows comparing the first coded genomic data and the second coded genomic data, or the first genomic block data and the second genomic block data in the encrypted state, and generating match data indexed by the first unique identification data and the second unique identification data.

3. The method as recited in claim 1, wherein at least one of the genomic block data or the genomic block allocation table is independently encrypted with a distinct encryption function or a distinct encryption key that differs from the function or key used to encrypt the first and second genome.

4. The method as recited in claim 1, wherein the second encryption key is identical to the first encryption key.

5. The method as recited in claim 1, wherein the portions of the first and second genomes encrypted are obtained by applying a selection function chosen by at least one user of the method.

6. The method as recited in claim 5, wherein designated locations for comparing the first and second genomes are obtained by applying a selection function chosen by at least one user of the method, and wherein generating the match data is based on comparing the selected portions of the first and second genomes, or the first coded genomic data and the second coded genomic data, or the first genomic block data and the second genomic block data, indexed by the first unique identification data and the second unique identification data.

7. The method as recited in claim 1, wherein the generating match data is an operation to measure or quantify the number of loci, strings, substring or genome subsequences of the first genome substantially matching the corresponding loci, strings, substring or genome subsequences of the second genome.

8. The method as recited in claim 1, wherein the generating match data is obtained by an operation to measure or quantify a percent identity of a number of designated loci of the first genome substantially matching corresponding loci of the second genome.

9. The method as recited in claim 1, further comprising a first user transmitting a request to at least one other user to compare genome data, and permitting the at least one other user to access the first user's coded genomic data or coded genomic block data, and sharing the at least one encryption function or the at least one encryption key applied by the first user to obtain coded genomic data or coded genomic block data.

10. The method as recited in claim 9, further comprising an invited user answering the request to compare genome data, and permitting the first user to access at least one of the match data, or the invited user's coded genomic data, or the invited user's coded genomic block data.

11. An electronic device comprising:
a processor; and
a memory storing instructions which, when executed, cause the processor to perform:
generating one or more unique identification data associated with a first genome;
generating at least one encryption key associated with the first genome;
indexing the at least one encryption key using the generated one or more unique identification data associated with the first genome;
generating one or more unique identification data associated with a second genome;
generating at least one encryption key associated with the second genome;
indexing the at least one encryption key using the generated one or more unique identification data associated with the second genome;
selecting at least part of the first and second genome;
encrypting at least part of the first genome into coded genomic data using the at least one first genome-associated encryption key;
encrypting at least part of the second genome into coded genomic data using the at least one second genome-associated encryption key;
indexing, respectively, the coded first and second genomic data using the at least one unique identification data associated with the first genome and second genome;
storing the encrypted first and second coded genomic data on the electronic device
dividing at least a portion of the first and second genome data into blocks;
generating genomic block data in response to indexing at least part of the first and second genome data in at least some data block by one of a genomic coordinate, an order, or genomic data content information;
storing at least a part of each genome block data in a corresponding genome block allocation table;
receiving requests to compare first genome and second genome, or first coded genomic data and second coded genomic data, or first and second genomic block data indexed by genomic coordinate, genomic data content information, or first and second coded or uncoded genomic data associated with phenotype, genotype, trait, disease, drug response, medical condition or behavior;
generating match data, by executing at the processor, instructions corresponding to the requested comparison; and
storing match data, indexed by the unique identification data corresponding to the compared genomes.

12. The electronic device as recited in claim 11, further comprising:
a transmitter configured to transmit the coded genomic data, or the match data, to an external device; and
a display communicatively coupled to the processor.

13. The electronic device as recited in claim 11, further comprising a receiver configured to receive genome data, coded genomic data, encryption keys, match data, or phenotype, genotype, drug response, disease, medical condition, trait or behavior data from at least one of a sample, an individual, or an organism, or from at least one other electronic device.

14. The electronic device as recited in claim 11, further comprising a database configured to store the coded genomic data, or match data, or both match and coded genomic data, indexed by the unique identification numbers associated with the coded genomic data, genomic block data, or compared genomes.

15. A system comprising;
a first electronic device comprising a processor and a memory, the memory storing instructions which, when executed, cause the processor to perform operations, including at least:
generating one or more unique identification data associated with genomic data,
generating at least one encryption key associated with genomic data,
indexing the at least one encryption key using the generated one or more unique identification data,
selecting at least part of the genomic data,
encrypting at least part of the genomic data using the at least one encryption key,
indexing the encrypted genomic data using the at least one unique identification data associated with the genomic data,
storing the encrypted genomic data on the electronic device,
dividing at least a portion of the genomic data into blocks,
generating genomic block data in response to indexing at least part of the genomic data in at least some data block by one of a genomic coordinate, an order, or genomic data content information, and
storing at least a part of the genomic block data in a block allocation table;
a second electronic device comprising a processor and a memory, the memory storing instructions which, when executed, cause the processor to perform operations, including at least:
receiving, at the electronic device, a request to compare a plurality of coded genomic data associated with a plurality of genomes or individuals,
determining common loci in the plurality of coded genomic data at which comparisons will be made,
comparing the plurality of encrypted genomic data at one or more designated common loci,
generating match data based upon the comparison of the plurality of coded genomic data, according the selected comparisons and associated measures or quantification of data attributes indicative of match occurrence or match probability, and
transmitting the match data; and
a display communicatively coupled to the first electronic device, the second electronic device, or both the first electronic device and the second electronic device.

16. The system as recited in claim 15, wherein the first electronic device further comprises a transmitter configured to transmit the block allocation table, genomic block data, the coded genomic data, one or more encryption keys associated with the coded genomic data, or some combination of the foregoing.

17. The system as recited in claim 15, wherein the first electronic device, or the second electronic device or both the first and second electronic device further comprises a receiver configured to receive genome data, coded genomic data, encryption keys, match data or phenotype, genotype, drug response, disease, medical condition, trait or behavior data from at least one of a sample, an individual, or an organism, or from the other electronic device.

18. The system as recited in claim 15, wherein the first electronic device, the second electronic device, or both the first electronic device and the second electronic device further comprise a database.

* * * * *